United States Patent [19]

Saferstein et al.

[11] Patent Number: 4,752,466
[45] Date of Patent: Jun. 21, 1988

[54] THROMBIN AEROSOL

[75] Inventors: Lowell Saferstein, Edison; Stephen J. Wolf, Manville, both of N.J.

[73] Assignee: Johnson & Johnson Products, Inc., New Brunswick, N.J.

[21] Appl. No.: 91,165

[22] Filed: Aug. 31, 1987

[51] Int. Cl.[4] ...................... A61K 9/14; A61K 35/14; A61K 37/00

[52] U.S. Cl. ........................................ 424/46; 424/45; 424/101

[58] Field of Search ...................... 424/40, 43, 44, 45, 424/47, 46, 101

[56] References Cited

U.S. PATENT DOCUMENTS

| | | | |
|---|---|---|---|
| 4,427,650 | 1/1984 | Stroetman | 424/46 |
| 4,427,651 | 1/1984 | Stroetman | 424/46 |

*Primary Examiner*—Nancy A. B. Swisher

[57] ABSTRACT

A process is disclosed for delivery thrombin in dry powdered form from an aerosol container by first lyophilizing an aqueous solution of thrombin and a thrombin-compatible synthetic polymer e.g. polyvinyl pyrrolidone, placing the lyophilized cake in a pressure bottle by crimping on a valve stem and top, filling liquified chlorofluoroalkane-containing aerosol propellant into the bottle, and actuating the valve to dispense in dry-finely divided powdered form a mixture of thrombin and polyvinyl pyrrolidone, which powdered thrombin is for use in controlling bleeding during surgery.

24 Claims, No Drawings

THROMBIN AEROSOL

This invention relates to thrombin and to a delivery system for delivering thrombin in dry powdered form from a pressurized, propellant-containing aerosol container, and is more particularly concerned with the process of lyophilizing a solution of thrombin and a thrombin-compatible synthetic polymer, preferably polyvinyl pyrrolidone (PVP) (Povidone U.S.P.), dissolving it in a chlorofluoroalkane propellant and dispensing the resultant thrombin-synthetic polymer mixture from an aerosol container, and to the compositions and containers obtained thereby.

BACKGROUND OF THE INVENTION

Thrombin is used to control oozing bleeding during surgery. It is frequently used in solution in which case the potency of thrombin is diminished by the dilution with aqueous saline. Some surgeons prefer to use thrombin as a dry powder, in which case they carefully tap the thrombin particles from the bottle onto the wound. A better delivery system for dry powdered thrombin would be an advantage for surgeons and is provided by the present invention.

PRIOR ART

It is known to dispense thrombin from an aerosol container, but only when certain desiccating and stabilizing agents and a fibrinolysis inhibitor are present also. The thrombin used must be reduced to very fine particle size by grinding procedures.

Stroetmann U.S. Pat. No. 4,427,651 teaches a sprayable preparation made with, in percent by weight, 15–60% Thrombin, 5–80% of a desiccating and stablizing agent, i.e. albumin, globulin and fibrinogen, 1–10% of a fibrinolysis inhibitor, e.g. an antiplasmin such as aprotinin, suspended in a low-boiling anhydrous solvent as propellant, e.g. various chlorofluro hydrocarbons e.g. Frigens, Freons, Dymels, Genetrons.

SUMMARY OF THE PRESENT INVENTION

By means of the present invention a way has now been found to dispense thrombin from an aerosol container without any desiccating and stabilizing agent (i.e. albumin, globulin and fibrinogen) except as they may exist as impurities in commercial thrombin or without any fibrnolysis inhibitor being present.

This invention provides a convenient way to deliver dry powdered thrombin directly to a wound, or directly onto a hemostat.

Dry powdered thrombin does not dispense readily from a conventional valve-actuated aerosol container because the thrombin particles are too large and clog the valve.

We have unexpectedly found that if the thrombin is first dissolved in an aqueous solution with a specific type of water soluble polymer, namely a "thrombin-compatible synthetic polymer" and then lyophilized, small particles of dry thrombin are produced. [A preferred example of such a water soluble polymer is polyvinyl pyrrolidone (PVP).] We have also unexpectedly found that if the lyophilized cake is placed in a pressure bottle with a propellant (which when liquified is a solvent for the polymer, or with a propellant that is a non-solvent for the polymer but which also contains a co-solvent that will dissolve the polymer), the thrombin particles will remain suspended in the liquified propellant and will be dispensed as a dry powdered spray from the aerosol bottle when the valve is actuated. The resultant dry powdered spray will contain fine particles of thrombin mixed with fine particles of the polymer, e.g. PVP.

Some advantages of this invention are that it allows thrombin to be dispensed as a dry powdered spray, thus permitting high potency dry thrombin particles to be placed directly on a wound or sprayed onto a hemostat. Also, the use of propellants such as low boiling chlorofluorocarbons leaves no traces of residual solvent and is safe for use with wounds. The thrombin aerosol package comes in a sterile, ready to use form requiring no preparation at the time of use. Small micron size particles of thrombin are required for a powder aerosol, and this invention produces the correct required particle size by freeze drying together an aqueous solution containing an appropriate minimum amount of polymer to thrombin potency. If no or not enough polymer is used, the freeze-dried particles of thrombin will be too large and will not dispense from the aerosol valves normally used.

It is known that small particles of thrombin can also be prepared by grinding operations such as a ball mill, but such type of procedure is not convenient for aseptic processing. The present invention circumvents the commutation step and allows mild conditions and aseptic preparation of a thrombin aerosol.

In a preferred embodiment, an aerosol glass bottle (which permitted visual inspection) containing thrombin and polyvinyl pyrrolidone was pressurized with Freon 12 and ethyl alcohol. The polyvinyl pyrrolidone dissolved and the thrombin remained suspended in the liquified propellant. When the actuator was depressed a fine spray of thrombin and PVP was obtained. The powder was dry to the touch.

DETAILED DESCRIPTION OF THE INVENTION

The thrombin aerosol of the present invention is intended for use in surgical applications in the body and therefore all ingredients used must be of an appropriate grade and purity, i.e. pharmaceutically acceptable grade.

The major materials to be used in the present invention are thrombin, the "thrombin-compatible synthetic polymer", e.g. PVP, and the propellant.

Thrombin:

Thrombin is defined in the U.S. Pharmacopoeia (1985) as a sterile, freeze-dried powder derived from bovine plasma containing the protein substance prepared from prothrombin through interaction with added thromboplastin in the presence of calcium. It is capable, without the addition of other substances, of causing the clotting of whole blood, plasma, or a solution of fibrinogen. Its potency is determined in U.S. Standard units in terms of the U.S. Standard thrombin in a test comparing clotting times of fibrinogen solution.

Thrombin U.S.P. is commercially available in the U.S. from several different manufacturers. Thrombin, Topical (bovine) U.S.P. is available as "Thrombinar" from Armour Pharmaceutical Company in several different potencies e.g. 1,000, 5,000, 10,000, 20,000, and 50,000 U.S. Standard unit vials, usually as a lyophilized white powder. That commercial product also contains 50 percent mannitol and 45% sodium chloride by weight.

Thrombin, Topical (bovine origin) is available as "Thrombogen" (Gen Trac Incorporated) and as "Thrombostat" (Parke-Davis) in potencies of 1,000, 5,000, 10,000 and 20,000 U.S. units. The commercial products also contain calcium chloride, sodium chloride, and glycine. They also appear as lyophilized white powders.

Any of the commercially available thrombin products can be used as starting materials for purposes of the present invention although the resultant aerosol products of the present invention obtained will differ slightly since the starting thrombin products differ slightly. Thrombin is an enzyme product derived from natural sources, and could contain other materials present in the bovine plasma from which it is prepared. It can vary in purity, potency, and other materials present, depending on the manufacturer.

The weight of thrombin as measured by its mass is very small with respect to its activity as measured by its U.S. units. For example a sample of 10,000 units of thrombin (Parke-Davis or GenTrac) weighed only 83 milligrams. If this 10,000 units of thrombin are dissolved in 100 ml. of water, there is a concentration of 100 U.S. units/ml. when expressed as activity per ml., but only 0.083% when expressed as grams of thrombin per 100 ml. of solution. Thus it is easier and customary to refer to the amount of thrombin from the standpoint of its activity, rather than its weight, in describing the invention. Thrombin is an enzyme, is usually impure, and what is important is its activity, not its weight.

Thrombin-Compatible Synthetic Polymer:

The "thrombin-compatible synthetic polymer" used in the present invention must be soluble in water and also in the particular propellant or propellant cosolvent used. SInce for one major intended use i.e., in surgery on internal organs it will be left in the body when sprayed from the aerosol container, the specific polymer has to be non-toxic, absolutely safe and not deleterious, and it must be capable of being eliminated from the human body by natural means so it does not remain there as an undesirable foreign object which could cause problems. Relatively few polymers are known which meet all the aforesaid necessary qualifications and the one which currently appears to be practical for that use is polyvinyl pyrrolidone (PVP), and its medical low molecular weight grades. For this reason we will mostly refer to PVP in describing the present invention, but it is to be understood that other polymers which meet all the necessary qualifications are to be regarded as the equivalent of PVP in this invention. In U.S. Pharmacopoeia XXI, Povidone is listed as being a synthetic polymer consisting essentially of linear 1 - vinyl - 2 - pyrrolidone groups, the degree of polymerization which results in polymers of various molecular weights. The particular polyvinyl pyrrolidones useful for inside-the-body surgical purposes of the present invention are low molecular weight polyvinyl pyrrolidones, of which two are currently commercially available, one having an average molecular weight of 10,000 and the other an average molecular weight of 40,000. Povidone U.S.P. (polyvinyl pyrrolidone) is made by GAF as "Plasdone C-15" and "Plasdone C-30", and is also made by BASF. The polyvinyl pyrrolidone appears in the form of a fine white powder.

There is commercially available a high molecular weight polyvinyl pyrrolidone having a molecular weight of 360,000 which cannot be used for certain purposes of the present invention since its molecular weight is too high to permit it to be excreted through the kidneys. It can be used for other purposes of the present invention i.e., for application to external body surfaces where it will not have to be so excreted. For such types of external surgical uses, various other polymers are the functional equivalents of high MW PVP and may be used in its place as long as they are soluble both in water and also in the propellant or propellant-cosolvent used, are non-toxic, are pharmaceutically acceptable, are not deleterious to thrombin, i.e. they do not denature the thrombin or bind it to make it unavailable, and they have a pH (in a 1% aqueous solution) of 5–8 i.e. a pH where thrombin is stable. Examples of such other copolymers include hydroxypropyl cellulose (available as Klucel from Hercules in various, preferably low and medium M.W. grades), polyehtylene oxide (available as Polyox from Union Carbide - preferably in low molecular weight grades e.g. 100,000–500,000 for use in the present invention, polymethyl vinyl ether, hydroxy ehtyl cellulose and hydroxymethylpropylcellulose. Synthetic polymers having all the above-defined properties are "thrombin-compatible synthetic polymers" for purposes of this invention.

Propellant:

The propellants used in the present invention to dispense the thombin from the pressurized container in the form of an aerosol are chlorofluoroalkanes, and are well known for such purposes. For use in the present invention the propellant must be non-toxic, leave no residue, and not have any adverse effect on body tissue. Various known chlorofluorocarbon propellants have been banned for general use in the United States for ecological reasons. They still may be useful for purposes of the present invention. Of those presently available, we prefer to use chlorodifluoromethane, which has the formula $CHClF_2$ and which is available commercially as Dymel 22 and Freon 22 from Dupont or as Genetron 141 from General Chemical. This particular material has a vapor pressure such that it can be used as the sole propellant for purposes of the present invention. Because its vapor pressure is relatively high, being 121.4 at 70 degrees F., a stainless steel aerosol container is normally used. It is possible to use other chlorofluoroalkanes, together with the chlorodifluoromethane (Dymel 22 or Freon 22) to lower the vapor pressure. It is known that anhydrous polyvinyl pyrrolidone is directly soluble in propellants containing a $CHX_2$ group (where X is a halogen), and that it will dissolve in several other chlorofluoroalkanes used in pressurized products if alcohol is used as a cosolvent. Successful results have been obtained by mixing trichlorofluoromethane (Freon 11 or Genetron 11) with Freon 22. Mixtures of 1-Chloro-1,1-Difluoroethane ($CH_3CClF_2$) (Dymel 142 or Freon 142) with Freon 22 have been successfully used, as have mixtures of Freon 22, Freon 142 with ethyl alcohol as a cosolvent. Among the other materials which could be used in propellant mixtures to lower the vapor pressure are isobutane, butane, propane, and various low boiling solvents including dimethyl ether, ethyl alcohol, methylene chloride, and methyl alcohol. Other usable propellant mixtures will be apparent to those skilled in the aerosol field. The use of such propellant mixtures results in a lower vapor pressure which will permit the use of aluminum or glass or other kinds of aerosol cans in place of steel aerosol cans which would otherwise be used.

Thrombin-Polymer Amounts:

The procedure used to make the thrombin aerosol of the present invention requires dissolving the thrombin in water to make a dilute solution. The amount of thrombin used will depend on the desired potency of what is to be sprayed from the aerosol container.

There are a number of factors to consider in determining how much synthetic polymer to use with the thrombin, as will now be discussed.

During the freeze drying of the thrombin polymer solution, enough water soluble polymer must be present to sufficiently disrupt the crystallization of the thrombin molecules and cause them to form as very fine particles. Said fine particles of thrombin will then readily disperse in the aerosol propellant solvent mixture, appearing as a milky suspension.

If an insufficient amount of polymer is present with the thrombin in the lyophilization step, the thrombin particles will freeze dry as large crystalline particles which will not suspend in the aerosol solvent and will not pass through the valve of the aerosol can.

It has been found that if the amount of polymer present is about at least 1 gram of polymer for every 10,000 U.S. units of thrombin fine particles of thrombin are produced during the freeze drying step Higher ratios of polymer to thrombin can also be employed with no detrimental effects, and will often be preferred.

The ability of the polymer to produce small particles of thrombin is proportional to the amount of polymer used and the molecular weight of the polymer. The higher the molecular weight of the polymer, the better its ability to prevent the crystallization of the thrombin during the freeze drying, so less of it is needed to do this.

The ability of the polymer to maintain the thrombin particles suspended in the aerosol solvent also depends to some extent on the molecular weight of the polymer, and its concentration in the solvent or solvent mixture. Low molecular weight polymers are not as efficient as high molecular weight polymers in suspending the fine thrombin particles and therefore more low molecular polymer is needed to achieve the same suspending ability as the high molecular weight polymer. For a polymer of a molecular weight less than 20,000 daltons, such as polyvinylpyrrolidone K-15 grade (GAF), at least 4 weight percent of polymer per weight of solution is needed in order to produce a stable milky suspension of the thrombin particles in the aerosol solvent. If less than a 4% polymer concentration is prepared, the thrombin particles will settle out of the solvent and the thrombin will not spray out of the aerosol can uniformly.

For polymers of a molecular weight greater than 20,000 but less than 50,000 daltons such as polyvinylpyrrolidone K-30, at least than 2% (weight percent of polymer per weight of solution) is needed to adequately suspend the throbin particles. For polymers of molecular weight higher than 50,000 daltons such as PVP K-90, or hydroxypropyl cellulose (Klucel, grade L) at least 0.5 weight percent is needed.

After the polymer-thrombin combination is freeze dried, the amount of aerosol propellant and co-solvent to be added to the thrombin polymer cake is determined according to the above stated factors to achieve a stable suspension of the thrombin particles in the aerosol can.

Using the illustration above, 10,000 units of thrombin will require no less than one gram of polyvinylpyrrolidone K-30 grade to effect small particles of thrombin during the lyophilization step. PVP grade K-30 has a molecular weight of 40,000, therefore no less than 2% solution should be made up in the aerosol propellant in order to maintain the thrombin particles in a suspension.

In the process of preparing the composition of the present invention, the above polymer thrombin adduct is added to an aerosol can and the valve crimped on. Then, through the valve stem there is added 49 grams of a mixture of propellants consisting of 60% by weight of Freon 11 and 40% by weight of Dymel 22. Thus the one gram of PVP is in a total of 50 grams of solution, e.g. a 2% PVP solution. The weight of the 10,000 units of thrombin or 66 milligrams is so small it can be ignored in the calculations. The aerosol can now contains 10,000 units of thrombin in 49 grams of propellant and one gram of PVP. The thrombin will remain suspended and will dispense uniformly with the propellant when the valve is depressed. Of course more PVP could have been used for the same amount of thrombin with no detrimental effects as long as the viscosity of the solvent is not increased so much that the solvent is too viscous to spray out of the can.

When using low MW PVP, which is the preferred polymer for internal surgical thrombin applications, we prefer to use more polymer, and generally employ at least one gram of polymer for every 5,000 U.S. Standard units of thrombin.

In the process of the present invention the first step is to prepare dilute solutions of thrombin and polymer in water. The purpose of using dilute solutions of both starting materials (thrombin and polymer) is so as not to precipitate the materials when the two solutions are combined, as could occur if concentrated solutions were used.

The next step of the process is to mix both the polymer e.g. PVP solution and the thrombin solution (which are each clear solutions) together to obtain a clear solution containing both PVP and thrombin. This combined solution is then frozen. A temperature below 0° C. is used, preferably −20° C. or colder. The frozen material is then put in a freeze-drier (lyophilizer), where a strong vacuum is turned on, e.g., 100 millitorrs, and is brought to room temperature. After about 24 hours of freeze drying, the water has sublimed off, and the resultant lyophilized product is a mixture or adduct of thrombin and PVP in the form of a white, spongelike, friable material.

The lyophilized mixture is placed in an open aerosol can or bottle, the valve stem and top are placed thereon and crimped into place. The amount of thrombin-PVP mixture used in each can could differ according to the potency desired, but typically might be on the order of magnitude of 0.5 to 1.0 gram.

The propellant, in liquified form, then is filled into the aerosol container through the valve from a tank where it exists in liquified form. The amount of propellant used typically might be on the order of 10 grams. [Other methods of filling an aerosol container are well known and may be used if desired]

Inside the aerosol container, the thrombin-compatible synthetic polymer e.g. PVP completely dissolves in the propellant. The thrombin does not dissolve, but exists in a very finely divided state, i.e., it is suspended in the propellant, where it exists as a finely divided milky suspension.

When the valve is depressed to spray the material from the aerosol container, a mixture of thrombin, PVP and propellant is emitted. The thrombin comes out as a dry white powder, mixed with the PVP which also comes out as a white powder. The propellant evaporates quickly and disappears. What is sprayed looks as though it were a single white powder, but is actually a mixture containing both PVP and thrombin, in the relative proportions in which they were inserted into the aerosol container. In other words, by weight there is much more PVP present than thrombin. In actual use in surgery, the thrombin serves as a hemostat which can be applied onto a surgical site to stop bleeding. The PVP has no adverse effect on the tissues and has a history of safe use in the body. Thus its use is not deleterious for the intended purpose of this invention. The same is also true for other thrombin-compatible synthetic polymers intended for use in the body.

Aerosol containers and components thereof designed for dispensing powder sprays are commercially available, and may be used in the present invention. In the "Handbook of Aerosol Technology" by Paul Sanders (Van Nostrand, Reinhold Company, N.Y. 1979, 2nd. ed. Chapter 21 entitled "Aerosol Suspensions) (Powders) gives helpful background information.

The aerosol package of the present invention should be prepared and handled in such manner that its contents will be sterile when sprayed. The use of bacterial filters and aseptic processing techniques results in a sterile product.

The aerosol of the present invention is designed to be stored in a refrigerated form. In this form it is relatively stable for at least for periods of 6 months in testing performed thus far. Since the thrombin in this invention is applied to tissues in a concentrated form, it has the advantage of being fairly potent as compared to the diluted form in which it is normally administered in non-aerosol form.

EXAMPLE 1

PVP-Thrombin-Laboratory Scale 10 grams of polyvinyl pyrrolidone K-30 (40,000 MW from GAF Corporation) were dissolved in 50 ml of distilled water, and the pH was adjusted to pH 7 with a few drops of dilute sodium bicarbonate. Separately, 50,000 U. S. Standard units of bovine thrombin (Thromogen freeze-dried thrombin made by GenTrac) were added to and dissolved in 145 ml of distilled water. The two solutions were combined and filtered through a sterile filter to remove any bacteria. 20 ml of the resultant sterile solution was added to each of 9 small (30 ml capacity) aluminum aerosol cans (available from Monobloc, size 22 mm×60 mm, having a Microflex lining), without tops, and the cans were placed in a lyophilizer. After freeze drying for 24 hours, a white powder was left in each of the 9 aerosol cans. An aerosol spray valve (Emson 5-20, with neoprene rubber gasket) was crimped onto each can, and thereafter each can was filled through the valve stem with an aerosol propellant consisting of 20 grams of a mixture of 60 percent by weight Freon 11 and 40 percent by weight Dymel 22 which had been previously passed through a sterile filter. [From previous experiments in glass pressure bottles it is known that the PVP polymer dissolved in the mixture of chlorofluorocarbon propellants leaving the thrombin remaining suspended as a fine milky suspension.] The pressure of the propellant gas within the aerosol can contained about 5,000 U.S. units of thrombin, 1.02 grams of the PVP polymer and 20 grams of the chlorofluorocarbon mixture propellant.

When the actuator of the aerosol can was depressed, a dry powder thrombin and PVP polymer mixture was sprayed which can be applied directly onto a wound. The propellant evaporated almost instantly. The resultant spray is very effective in stopping bleeding on cuts, scrapes and in internal surgery on oozing bleeding.

The thrombin in these cans was stable for at least 6 months when refrigerated at 4° C.

EXAMPLE 2

PVP-Thrombin-Bulk

This is an example of a bulk manufacturing technique.

A stainless steel 1 liter Parr bomb pressure container was charged with 13.5 grams of ethyl alcohol, 194.6 grams of Dymel 142 and 291.9 grams Dymel 22, resulting in a mixture of solvents consisting of, in percent by weight, 2.7 percent ethyl alcohol, 38.9 percent Dymel 142 and 58.3 percent Dymel 22. Another stainless steel 1 liter Parr bomb pressure container was charged with 40,000 U.S. units of thrombin dissolved in 116 grams of water. Separately, 7.8 grams of polyvinyl pyrrolidone K-30 (GAF Corporation) in 40 grams of water had its pH adjusted to 5.9 using a 1% sodium bicarbonate solution, and the PVP solution was added to the thrombin solution in the Parr bomb. The thrombin-PVP solution is removed from the Parr bomb and sterile filtered, using a bacterial filter, and put back in the Parr bomb pressure vessel. The pressure vessel is then placed in a lyophilizer and freeze dried. After freeze drying the pressure vessel contains 40,000 units of thrombin in 7.8 grams of PVP (5,128 U.S. units per gram of PVP). The two pressure vessels were connected using a stainless steel coupling hose. 170 grams of the sterile filtered mixture of solvents from the first pressure vessel is added to the freeze dried PVP-thrombin powder. The PVP-thrombin containing pressure vessel is placed on a scale, and the valve opened to allow the solvent to be added in the desired amount. The PVP dissolves in this mixture of solvents leaving the thrombin remaining as a finely divided suspension. From this bulk source, three aerosol cans were filled through the valve stem with 20 grams each of the thrombin suspension. The resultant aerosol cans contained at least 4,000 units of thrombin. The pressure of the propellant gases in the filled aerosol cans was about 80 pounds per square inch. The thrombin contents were stable for at least 6 months when refrigerated at 4° C.

In Examples 1 and 2 stability of the thrombin was measured by assaying the thrombin sprayed from the aerosol container periodically and finding that it retains at least 90 percent of its starting potency. Potencies below this figure are considered unstable. The tests are still proceeding and the aerosol contents may be stable for longer periods of time.

EXAMPLE 3

Hydroxypropyl Cellulose-Thrombin

Into 20 ml of water there was disclosed 0.5 grams of hydroxypropyl cellulose [Klucel (LF grade)]. The ph was adjusted to 7.0 with a 0.5% sodium bicarbonate solution. Into 5 ml of water there was dissolved 5,000 units of Thrombogen thrombin from GenTrac. The thrombin solution was added to the Klucel solution. A clear homogeneous solution resulted. This was freeze dried over a 16 hour period to give a Klucel sponge of about 0.5 grams containing 5,000 units of thrombin. The sponge was placed in an aerosol bottle and a valve crimped on. Through the valve stem was added 10 grams Dymel A and 2 grams ethyl alcohol. [Klucel is not soluble in Dymel A alone but is soluble in ethyl alcohol. The Klucel polymer is soluble in the mixture of ethyl alcohol and Dymel A. The Dymel A is basically the propellant and the ethyl alcohol the solvent for the Klucel] The thrombin remained suspended in this milky white aerosol. The vapor pressure was 50 psig. When the actuator was depressed a powder spray of thrombin and Klucel along with the solvent are released. This aerosol is an effective way of delivering thrombin to topical burns, cuts, and scrapes.

What is claimed is:

1. The process of delivering thrombin in dry powdered form from a valve-actuated, pressurized, propellant-containing aerosol container comprising the following steps:
   (a) lyophilizing an aqueous solution of thrombin and a thrombin-compatible synthetic polymer
   (b) placing the resultant lyophilized thrombin-compatible synthetic polymer mixture into a valve-actuated aerosol container together with a liquified chlorofluoroalkane-containing aerosol propellant, and
   (c) actuating the valve, 2. The process of claim 1 wherein the thrombin-compatible synthetic polymer used is polyvinyl pyrrolidone, hydroxypropyl cellulose, polyethylene oxide, polymethyl vinyl ether, hydroxyethyl cellulose or hydroxymethylpropylcellulose.

3. The process of claim 2 wherein the thrombin-compatible synthetic polymer is polyvinyl pyrrolidone which is present in an amount of at least one gram for every 10,000 U.S. units of thrombin.

4. The process of claim 3 wherein the polyvinyl pyrrolidone is a low molecular weight polyvinyl pyrrolidone.

5. The process of claim 1 wherein an aqueous solution of thrombin is mixed with a separate aqueous solution of polyvinyl pyrrolidone as the thrombin-compatible synthetic polymer used to form the aqueous solution which is lyophilized in step (a).

6. The process of claim 1 wherein the liquified chlorofluoroalkane-containing aerosol propellant comprises (a) chlorodifluoromethane or (b) chlorodifluoromethane combined with a cosolvent or (c) chlorodifluoromethane combined with a different chlorofluoroalkane propellant.

7. The process of claim 6 wherein the liquified chlorofluoroalkane-containing aerosol propellant used has a vapor pressure suitable for use in stainless steel or in aluminum aerosol cans.

8. The process of claim 1 wherein all ingredients and components used are pharmaceutically acceptable and the final package contents are sterile.

9. The process of spraying a mixture of thrombin and thrombin-compatible synthetic polymer in dry powdered form from a valve-actuated pressurized, propellant-containing aerosol container comprising the following steps:
   (a) lyophilizing an aqueous solution of thrombin and a thrombin-compatible synthetic polymer;
   (b) placing the resultant lyophilized thrombin-compatible synthetic polymer mixture into a valve-actuated aerosol container together with a liquified chlorofluoroalkane-containing aerosol propellant; and
   (c) actuating the valve.

10. The process of claim 9 wherein the thrombin-compatible synthetic polymer used is polyvinyl pyrrolidone, hydroxypropyl cellulose, polyethylene oxide, polymethyl vinyl ether hydroxypropyl cellulose or hydroxymethylpropylcellulose.

11. The process of claim 10 wherein the thrombin-compatible synthetic polymer is polyvinyl pyrrolidone, which is present in an amount of at least one gram for every 10,000 U.S. units of thrombin.

12. The process of claim 11 wherein the polyvinyl pyrrolidone is a low molecular weight polyvinyl pyrrolidone.

13. The process of claim 9 wherein an aqueous solution of thrombin is mixed with a separate aqueous solution of polyvinyl pyrrolidone as the synthetic polymer used to form the aqueous solution which is lyophilized in step (a).

14. The process of claim 9 wherein the liquified chlorofluoroalkane-containing aerosol propellant comprises (a) chlorodifluoromethane or (b) chlorodifluoromethane combined with a cosolvent or (c) chlorodifluoromethane combined with a different chlorofluoroalkane propellant.

15. The process of claim 14 wherein the liquified chlorofluoroalkane-containing aerosol propellant used has a vapor pressure suitable for use in stainless steel or in aluminum aerosol cans.

16. The composition of claim 15 wherein all ingredients and components used are pharmaceutically acceptable and the final package contents are sterile.

17. The process of claim 9 wherein all ingredients and components used are pharmaceutically acceptable and the final package contents are sterile.

18. A composition useful for spraying thrombin in dry powdered form from a pressurized aerosol container consisting essentially of thrombin and a thrombin-compatible synthetic polymer, which have each been lyophilized, incorporated in a low boiling liquified chlorofluoroalkane-containing aerosol propellant.

19. The composition of claim 18 wherein the thrombin-compatible synthetic polymer used is polyvinyl pyrrolidone.

20. The composition of claim 19 wherein the contents of the valve-actuated pressurized, propellant-containing aerosol container were obtained by the following steps:
   (a) lyophilizing an aqueous solution of thrombin and polyvinyl pyrrolidone
   (b) placing the resultant lyophilized thrombin-polyvinyl pyrrolidone mixture into a valve-actuated aerosol container together with a liquified chlorofluoroalkane-containing aerosol propellant.

21. The composition of claim 19 wherein the polyvinyl pyrrolidone used is low molecular weight polyvinyl pyrrolidone.

22. The composition of claim 21 wherein the polyvinyl pyrrolidone is present in an amount of at least one gram for every 10,000 U.S. units of thrombin.

23. The composition of claim 20 wherein an aqueous solution of thrombin is mixed with a separate aqueous solution of polyvinyl pyrrolidone to form the aqueous solution which is lyophilized in step (a).

24. The composition of claim 20 wherein the liquified chlorofluoroalkane-containing aerosol propellant comprises (a) chlorodifluoromethane or (b) chlorodifluoromethane combined with a cosolvent or (c) chlorodifluoromethane combined with a different chlorofluoroalkane propellant.

* * * * *